United States Patent [19]
Eden et al.

[11] Patent Number: 5,232,839
[45] Date of Patent: Aug. 3, 1993

[54] DETECTING MICROBIOLOGICAL GROWTH

[75] Inventors: Gideon Eden; Nadine M. Sullivan, both of Ann Arbor, Mich.

[73] Assignee: Difco Laboratories Incorporated, Ann Arbor, Mich.

[21] Appl. No.: 870,792

[22] Filed: Apr. 16, 1992

Related U.S. Application Data

[63] Continuation of Ser. No. 538,140, Jun. 14, 1990, abandoned.

[51] Int. Cl.$^5$ .......................... C12Q 1/04; C12Q 1/06; C12M 1/34; C12M 1/24
[52] U.S. Cl. ........................................ 435/39; 435/34; 435/287; 435/291; 435/296
[58] Field of Search ..................... 435/34, 39, 40, 287, 435/289, 291, 296, 807; 422/68.1, 82.13; 604/404

[56] References Cited

U.S. PATENT DOCUMENTS

| | | | |
|---|---|---|---|
| 3,837,745 | 9/1974 | Acker et al. | 435/291 |
| 3,907,646 | 9/1975 | Wilkins et al. | 435/34 |
| 4,152,213 | 5/1979 | Ahnell | 435/34 |
| 4,263,405 | 4/1981 | Melnick et al. | 435/291 |
| 4,314,029 | 2/1982 | Ohtake et al. | 435/291 |
| 4,952,498 | 8/1990 | Waters | 435/296 |
| 5,047,331 | 9/1991 | Swaine et al. | 435/34 |
| 5,051,360 | 9/1991 | Waters | 435/34 |

Primary Examiner—Robert J. Warden
Assistant Examiner—T. A. Trembley
Attorney, Agent, or Firm—Reising, Ethington, Barnard, Perry & Milton

[57] ABSTRACT

In such a method and apparatus for detecting microbiological growth in a sealed sample container, pressure within the headspace of the container is monitored for detecting rate of change of such headspace pressure. Presence of microbiological growth within the container is indicated as a function of rate of change of headspace pressure. The rate of pressure change is compared with a standard rate for a family of microorganisms., and growth is indicated when the absolute value of the rate of pressure change (which may be positive or negative) exceeds the absolute value of the standard rate (which also may be positive or negative). For detecting microbiological growths which may have differing growth rates, absolute value of rate of pressure change is compared to a plurality of standard rates for differing families of microorganisms. At least some of the rates may be positive, corresponding to growth of gas-producing organisms, and at least some of the rates may be negative, corresponding to growth of gas-consuming organisms. In either case, microbiological growth in the test sample is indicated when absolute mathematical value of the rate of headspace pressure change exceeds absolute mathematical value of any of the standard rates.

20 Claims, 9 Drawing Sheets

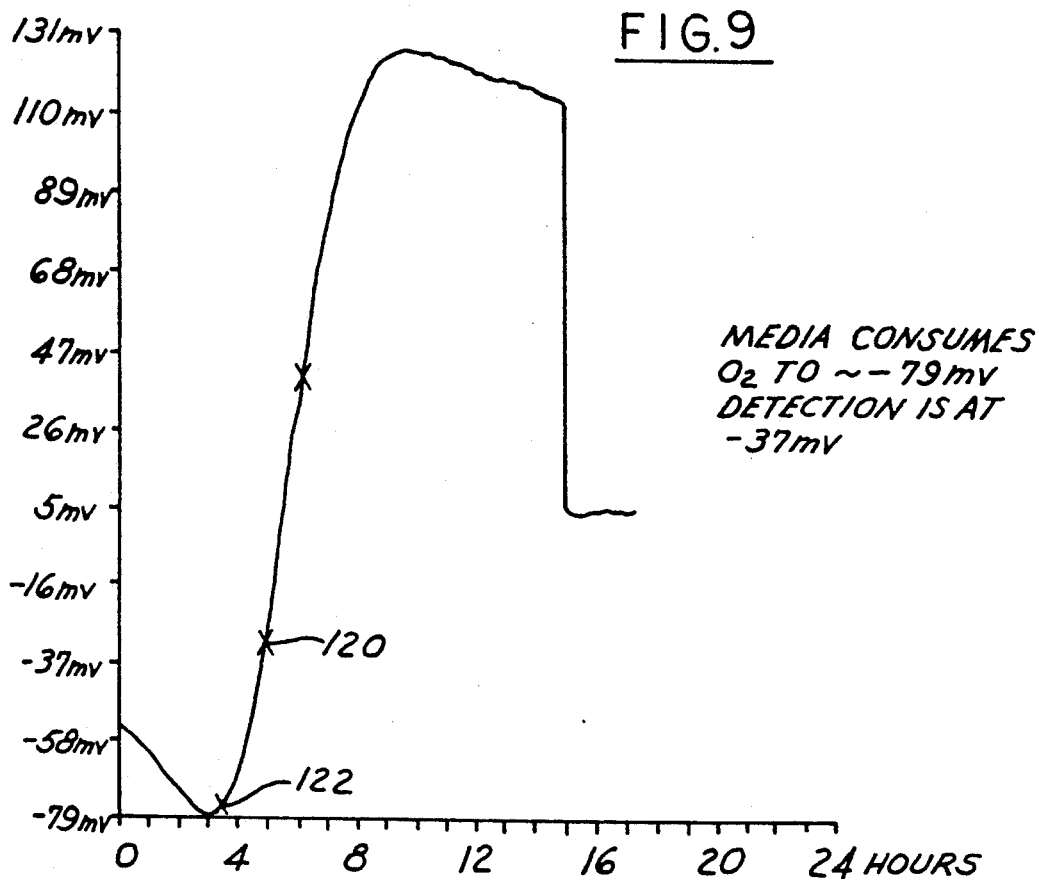
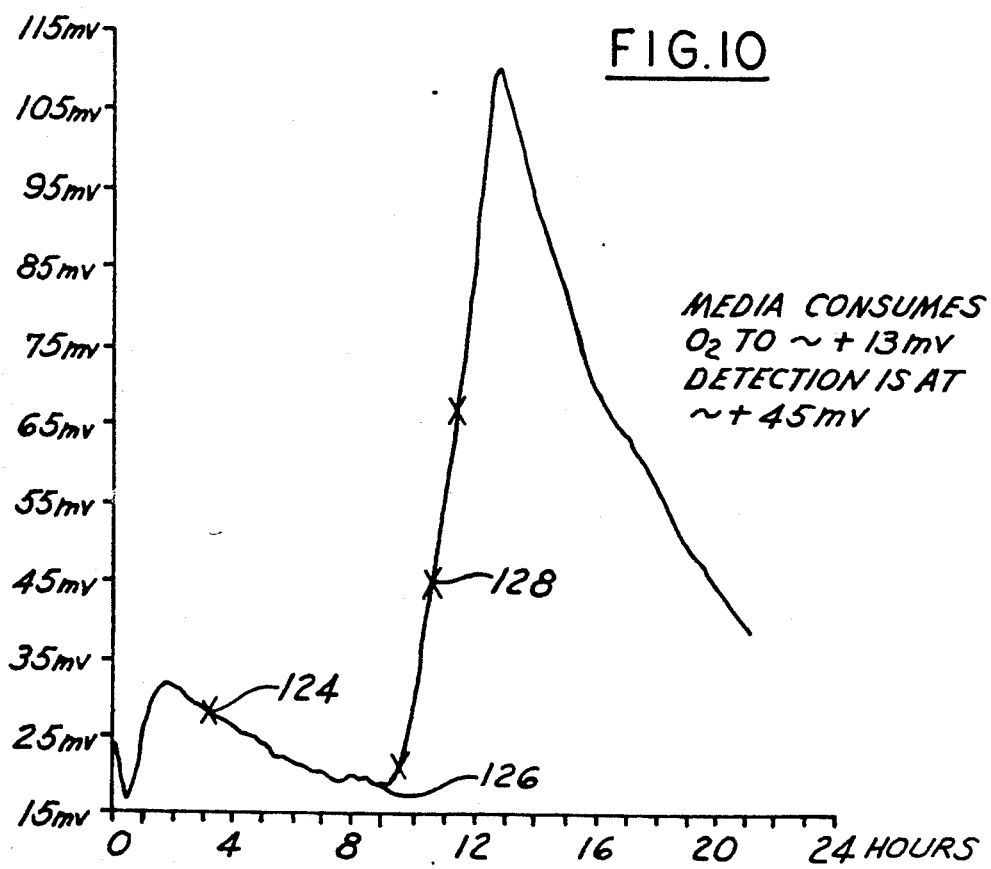

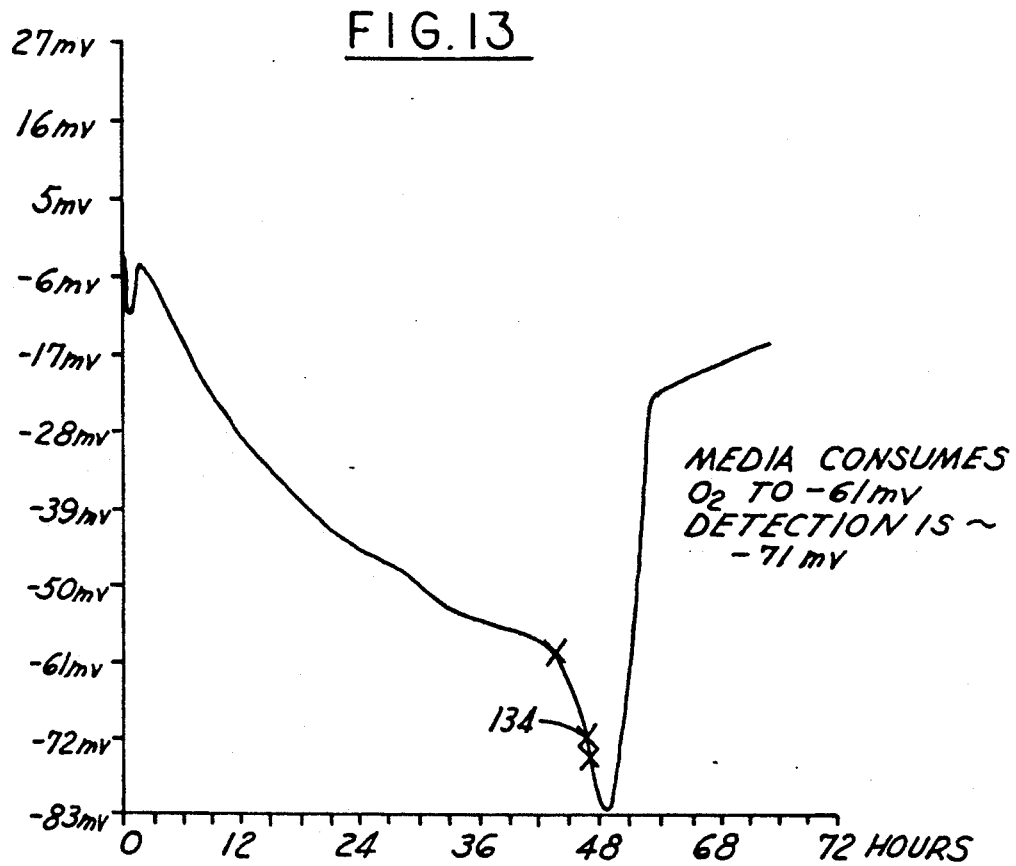
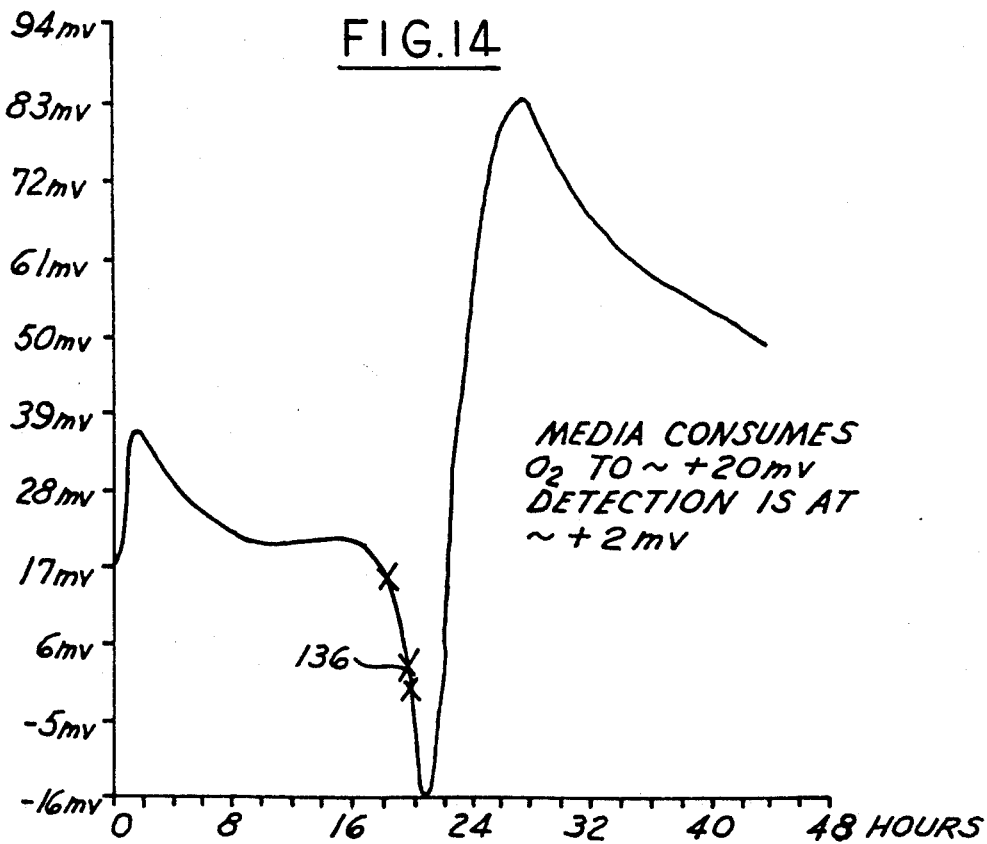

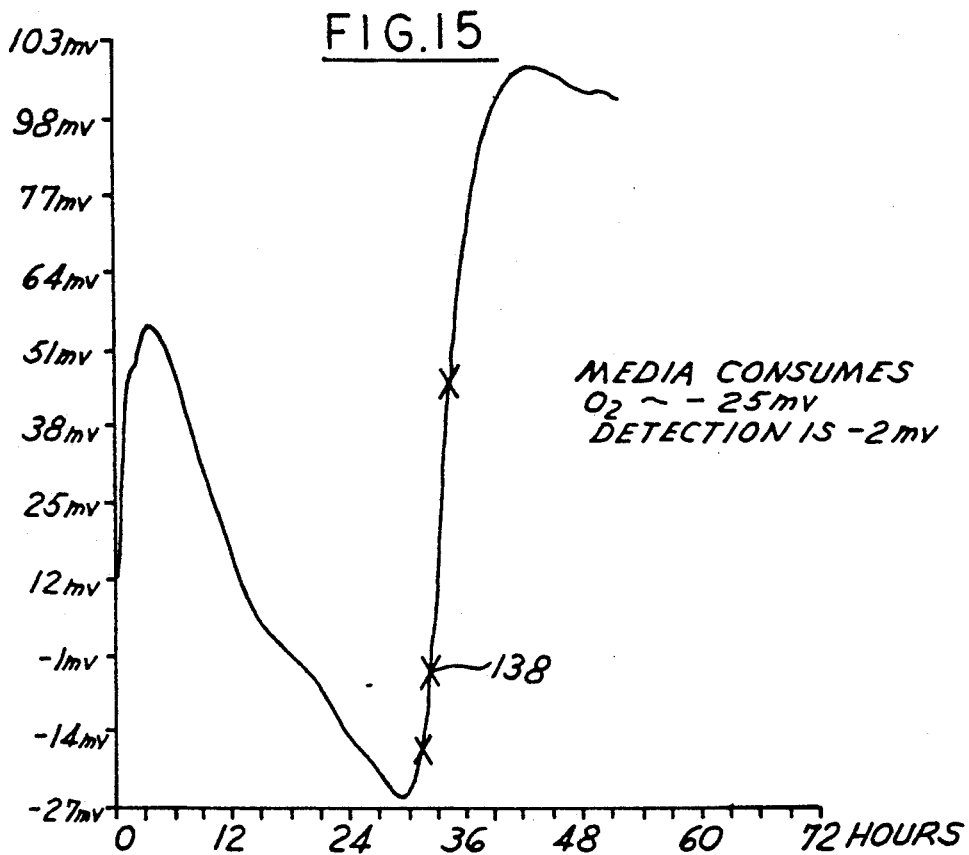
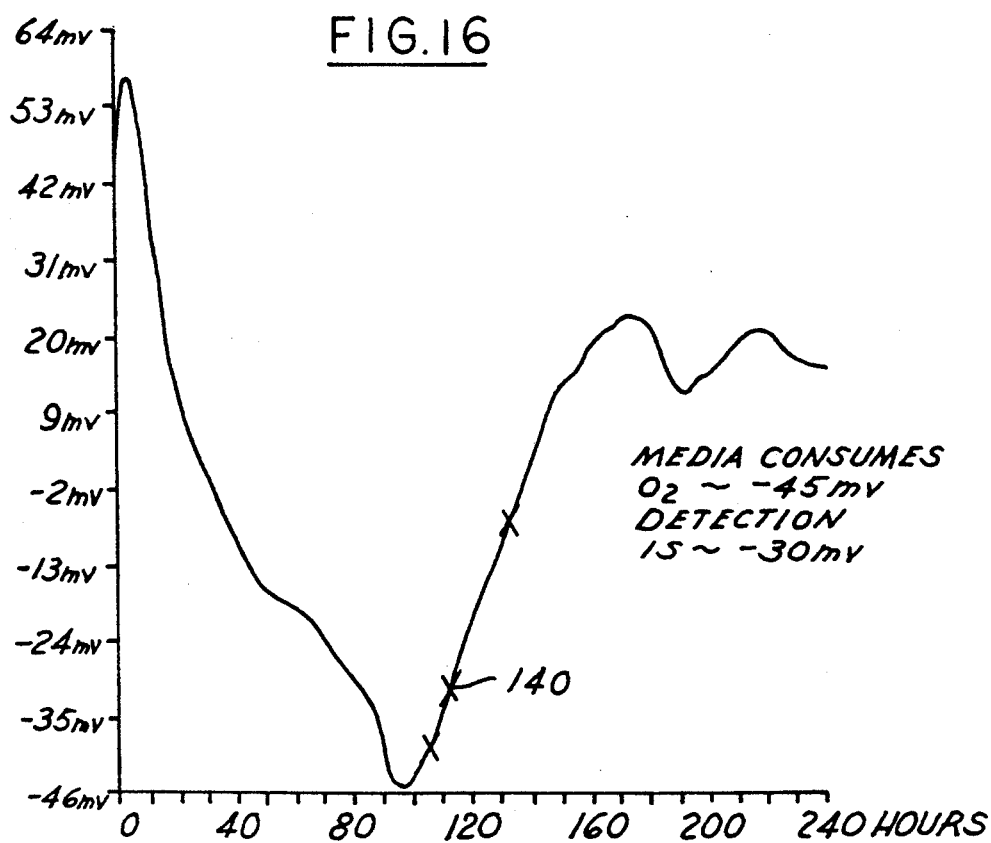

DETECTING MICROBIOLOGICAL GROWTH

This application is a continuation of U.S. Ser. No. 538,140, filed Jun. 14, 1990, now abandoned.

This invention relates to detecting microbiological growth, and particularly the presence of microorganisms in bodily fluids.

BACKGROUND AND SUMMARY OF THE INVENTION

In the medical field it is important to be able to determine whether or not normally sterile bodily fluids, such as blood, contain microorganisms. The presence of microorganisms in blood samples is indicative of a serious infection and can be life-threatening if not detected in a timely fashion.

There are several methods in current use to detect microorganisms. In manual systems, a sample of material to be tested is incubated, usually in a suitable growth medium. Various manipulations such as agitation are required during the incubation and monitoring period. The detection of growth is achieved by visual inspection. For example, technicians observe and assess the growth of bacteria on a Petri dish, or evaluate the clarity of a broth (turbidity). The visual observations and assessments are subjective and, therefore, subject to error. In addition, these manual methods are labor intensive, require significant manipulation, and entail observation of all samples by laboratory personnel.

A number of methods have been suggested to detect the presence or absence of microorganisms by less subjective means. U.S. Pat. No. 3,743,581 (1973), Cady et al, discloses a method for monitoring microbiological growth by measuring the change in the conductivity of selected nutrient media inoculated with a sample. This method reduces inaccuracies arising from human observation of organism growth. However, the method is relatively costly. In addition, it is relatively complex because temperature variations and movement or turbulence adversely affect this method. This is a disadvantage because optimal growth rates of microorganisms occur by shaking or agitating the cultures. Inasmuch as this method relies on conductivity, the media and sample must be stationary during measurement. On the other hand, optimal growth may occur when the cultures are agitated, known in the art as shaking cultures, which is done in an appropriate apparatus for shaking the container.

U.S. Pat. No. 3,907,646 (1975), Wilkins et al, describes measurement of gas production of microorganisms. A pressure transducer is applied to a test tube and connected to a power source and strip recorders. Measurements are recorded on the strip recorders producing a plot of an electrical signal, which is generated over time, indicative of the presence and quantity of microorganisms. The instrument is very large and cumbersome, making it impractical to monitor multiple samples.

In European Patent No. 0124193, the method for observing the growth of bacteria in a sample includes introducing a sample into a growth medium in a closed vessel, incubating the sample for a period of time, namely 18 hours, causing a change in pressure to force liquid through a needle into a chamber where the change in liquid level can be observed. The volume change can be observed in a number of different ways, including using a simple syringe to give a visual indication of a volume change in the sample of liquid without the need for any electronic equipment (see page 2, lines 5-8). A volume change can also be observed by visually detecting the volume change of liquid in a coiled tube connected to the hypodermic needle. In all the alternative embodiments described in the '193 patent, the needle of a syringe is caused to pierce the closure of the bottle to a level below the liquid in the bottle, whereby a pressure increase forces liquid into a cylinder of the volume indicating device. This is an indirect method to monitor a volume change because the volume change in the head space exerts a force which must be transmitted to the liquid causing the liquid to rise up into the needle. In Example I, the monitoring of volume change in liquid level is applied to a transducer. If the sample is shaken or agitated during the test, as is conventional, the gas in the headspace could pass through the needle above the liquid level and not produce a signal. If there were ambient temperature or pressure changes, the liquid level would change. Thus, in order to know if there has been any such change, the operator must continuously visually monitor the test, which is very impractical. Moreover, the operator cannot be certain what has caused a change, namely a temperature, atmospheric pressure, or growth of microorganisms. Therefore, a false reading may result.

U.S. Pat. No. 4,152,213 describes a system by which the growth of microorganisms in a sealed container is detected by measuring reductions in headspace pressure as the microorganism consumes oxygen and comparing the reduction in pressure to a reference standard of the initial pressure. A vacuum sensor senses a reduction in pressure in the headspace of a container and provides an electrical signal to remote electronics. A major problem with such a system is that it is limited to those organisms that consume oxygen. Many microorganisms do not consume oxygen. Thus, the presence of a vacuum is not a universal indicator of microbial growth. Another problem with such a system is that in many instances the maximum decrease in the headspace pressure is small in comparison to the natural variations of the atmospheric pressure. In addition, this method requires precise pressure sensors since it functions on the basis of absolute value of initial and threshold pressures.

Among the objectives of the present invention are to provide a method and apparatus for detecting the presence of microorganisms in bodily fluids that directly monitor the rate of change in the pressure in the head space above a sample to provide an indication of the microbial growth in the sample; that distinguish and correct for changes in atmospheric pressure; that detect both microorganisms which grow and produce gas or consume oxygen, such that both oxygen consuming and non-oxygen consuming microbial growth can be detected; that detect growth in both microorganisms which have rapid growth and microorganisms which have slow growth; that utilize electronics to detect such mechanisms; that are embodied in a self-contained and simple integral device that fits onto the neck of a bottle or container holding the sample; wherein the self-contained device comprises a disposable fitment and sleeve which covers the cap of the sample bottle and a hypodermic needle; which includes an electronic device including a sensor and electronics removably fitted on the disposable fitment.

In accordance with one aspect of the invention, the method of detecting microorganisms comprises the following steps:

1. Providing a sterile vial or bottle which is filled with a sterile liquid culture medium, the culture medium containing a combination of nutrients particularly adapted for use in detecting aerobic microorganisms or anaerobic microorganisms, as the case may be. The sterile vial is closed by means of an inert gas impermeable closure stopper, such as a rubber closure. The manufacturing process for the nutrient media produces a vacuum within the bottle. This vacuum allows for directly drawing of a specimen, such as a blood sample from a patient.

2. Inserting the bodily fluid, which is to be subjected to the detection of microorganisms, into the vial utilizing a hypodermic syringe or similar device forced through the rubber stopper.

3. Positioning a disposal fitment that includes a collar and a needle over the vial while forcing the hypodermic needle of the device through the closure so that the top of the needle is in the headspace above the liquid culture medium.

4. Positioning an electronic device on the fitment and activating the electronics to periodically monitor the rate of change of pressure which may have occurred due to the presence of microorganisms. If the pressure variation exceeds a predetermined rate of change of pressure due to growth of microorganisms, a signal or alarm is activated. A microprocessor analyzes the absolute value of the rate of change of pressure and compares the rates of change of pressure successively with stored rates of change representing aerobic organisms and anaerobic organisms which have differing rates of change of pressure and either are gas producing and gas consuming, and determines whether the rates of change represent organism growth or extraneous changes such as temperature or atmospheric pressure.

Another object of the present invention is to provide a method and apparatus for detecting microbiological growth in a sealed sample or test container that are adapted for employment in conjunction with monitoring either a single sample container or a multiplicity of sample containers, that are amenable to microprocessor-based implementation for enhanced economy, reliability and reduced size, that are adapted for use in detecting growth of both aerobic and anaerobic microbes, that readily accommodate both microbes that produce relatively rapid change of container headspace pressure and microbes that change headspace pressure more slowly, that may be employed by relatively unskilled operators with little or no operator intervention, and that are adapted in a single implementation for detecting growth of microbes of a variety of types and growth rates.

In such a method and apparatus for detecting microbiological growth in a sealed sample container in accordance with one presently preferred implementation of the invention, pressure within the headspace of the container is monitored for detecting rate of change of such headspace pressure. Presence of microbiological growth within the container is indicated as a function of rate of change of headspace pressure. The rate of pressure change is compared with a standard rate for a family of microorganisms, and growth is indicated when the absolute value of the rate of pressure change (which may be positive or negative) exceeds the absolute value of the standard rate (which also may be positive or negative). For detecting microbiological growths which may have differing growth rates, the absolute value of rate of pressure change is compared to a plurality of standard rates for differing families of microorganisms. At least some of the rates may be positive, corresponding to growth of gas-producing organisms, and at least some of the rates may be negative, corresponding to growth of gas-consuming organisms. In either case, microbiological growth in the test sample is indicated when absolute mathematical value of the rate of headspace pressure change exceeds absolute mathematical value of any of the standard rates.

In the preferred embodiments of the invention, headspace pressure is monitored by positioning a pressure sensor so as to develop an electrical pressure signal that varies as a function of headspace pressure within the container. The pressure signal is sampled and stored at preselected periodic time intervals, and successive signals are compared to each other to determine rate of pressure change. Preferably, each sampled pressure signal is compared to a pressure signal sampled and stored a predetermined number of time intervals previously. In this way, gradual rates of pressure change are detected. Most preferably, each sampled signal is compared to at least two signals sampled and stored differing predetermined numbers of intervals previously so as to determine rates of pressure change over differing time intervals.

The detection method and apparatus so described possess a number of significant advantages over prior art techniques. For example, use of rate of absolute value of the pressure change rather than absolute value of container pressure helps eliminate false growth indications due to changes in ambient pressure, temperature or other like conditions. In the same way, comparison of rate of actual pressure change to one or more predetermined standard growth rates helps eliminate false or erroneous growth indications, while at the same time rendering the invention amenable to detection of growth at differing rates, and to detection of growth of both aerobic and anaerobic microbes. In the same way, determination of rate of absolute value of the pressure change by comparison of current pressure with pressure at differing preceding times helps accommodate differing growth rates in both aerobic and anaerobic microbes.

BRIEF DESCRIPTION OF THE DRAWINGS

FIGS. 9-16 are graphic illustrations of pressure change in sample containers for various types of microbes detectable in accordance with the present invention.

DESCRIPTION

Figure 1:
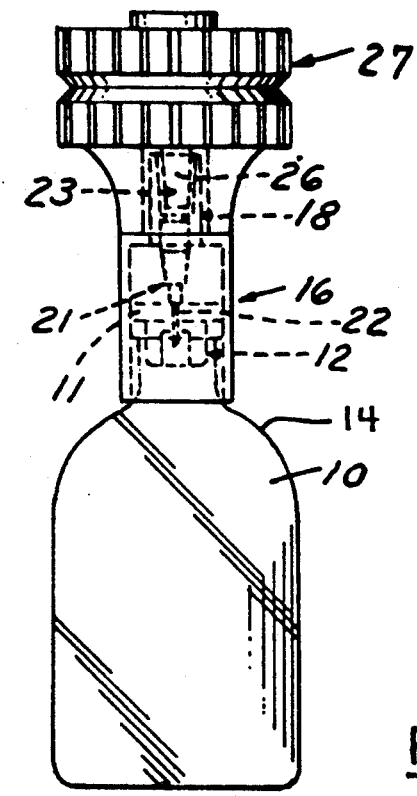
FIG. 1 is an elevational view of the assembly embodying the invention.
Figure 2:
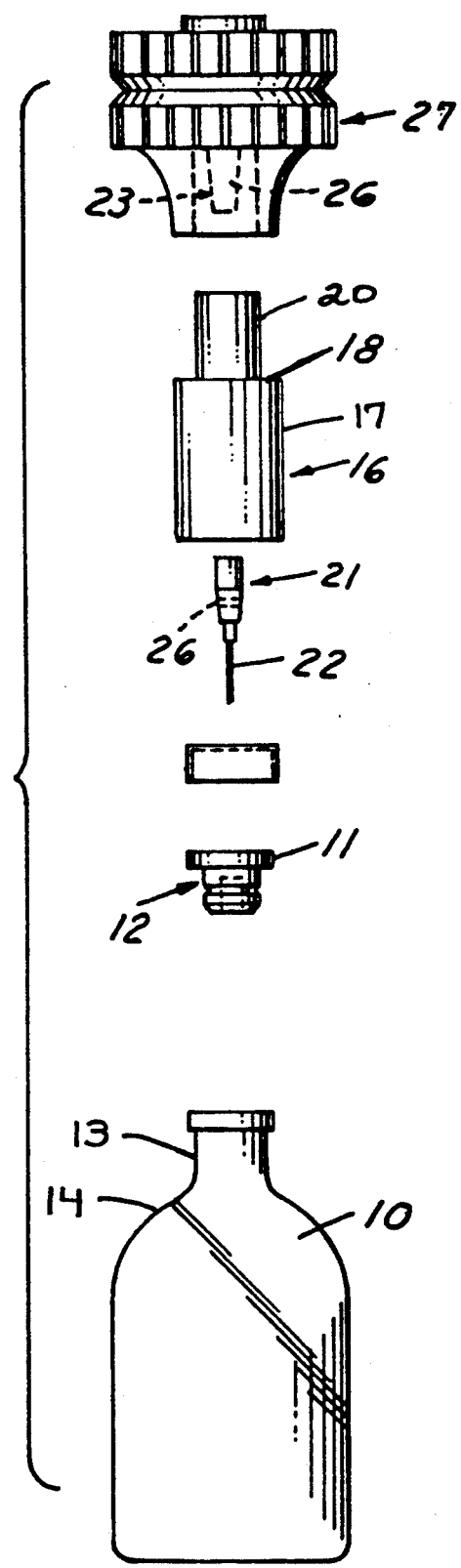
FIG. 2 is an exploded view of a culture container and pressure sensing device embodying the invention.
Figure 3:
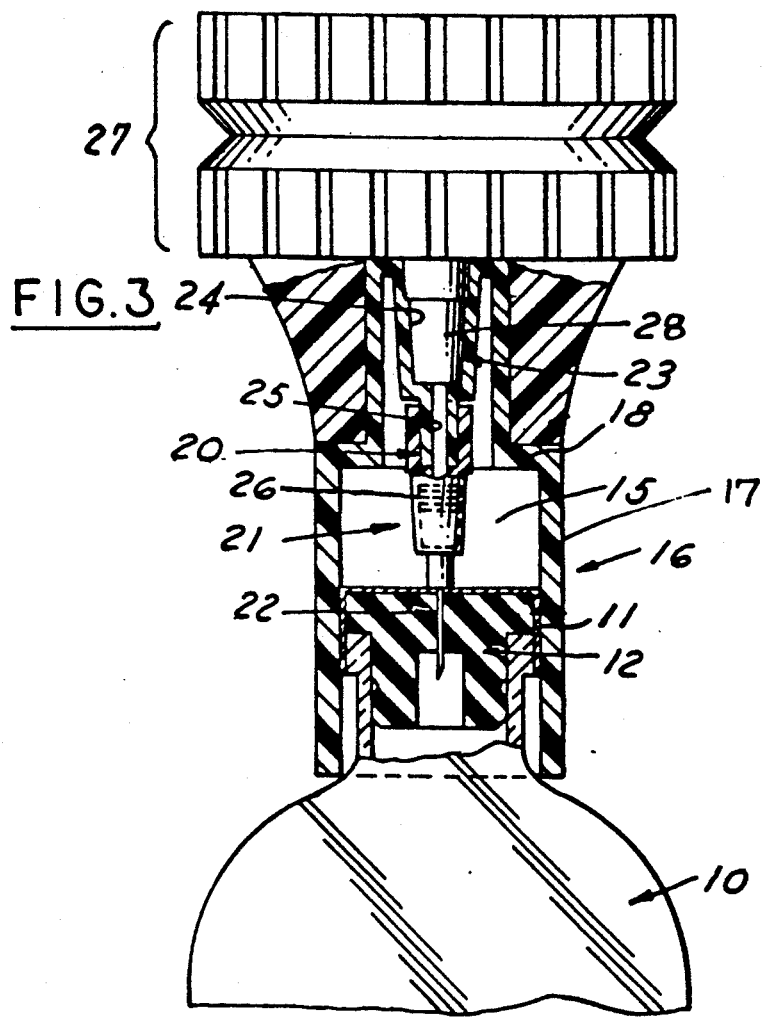
FIG. 3 is a fragmentary sectional view on an enlarged scale of the disposable fitment.

Referring to FIGS. 1-3, in the performance of the method, the vial or container 10 is of well known construction such as a glass bottle having a cap 11 with a resilient rubber stopper 12 that is exposed at its upper end. The container 10 is filled with either an aerobic or anaerobic culture medium depending upon the microorganism which is to be detected prior to application of the cap 11. The container 10 includes a neck 13 and a shoulder 14.

After the bodily fluid to be tested is inserted by a hypodermic needle through the stopper 12, a disposable plastic fitment 15 comprising a sleeve 16 is telescoped over the neck 13 of the container 10 so that the lower end of the sleeve 16 engages the shoulder 14 (FIG. 2). The sleeve 16 includes a tubular portion 17 and a top wall 18. The sleeve 16 further includes an integral tubular projection 20 onto which the hub 21 of a hypodermic needle 22 is frictionally and sealingly supported (FIG. 3). An integral tubular portion 23 extends upwardly from sleeve 16 and is formed with an opening 24 communicating with the opening 25 of the projection 20. A hydrophobic vent filter 26 is provided at the hub 21 of the needle 22. The filter 26 functions to prevent liquid from passing upwardly. The vent filter 26 is combined with the protective sleeve and needle assembly to provide the following functions:

1. To provide a bi-directional gas flow from the vial headspace to a pressure sensor during measurement or to the ambient during the initial or the final venting stages.
2. To prevent any liquid flow from the vial to the sensor or the ambient thus protecting the operator from bacterial or viral contamination.

The vent filter 26 can be either a depth or screen filter. A depth filter is characterized by a matrix of randomly oriented fibers or beads pressed, wound or otherwise bonded together into a maze of flow channels. A screen filter is formed by a rigid, uniform continuous mesh of polymeric material with well-defined pore size.

To prevent any liquid flow, the filter 26 is made of hydrophobic material, i.e., moisture repellent. The pore size and the type of material determine the liquid break pressure which should be adjusted to the region of several pounds per square inch (e.g. hydrophobic glass laminate with 0.3 micron pore size). The fitment 15 including needle 22 thus forms an integral disposal unit that can be placed on the upper end of a container 10. The fitment 15 is made of plastic which can be sterilized.

The fitment 15 is adapted to be connected to a tubular projection 28 on a removable electronic sensor unit 27 so that it is sealingly engaged with the portion 23. The electronic unit includes a pressure sensor and is preferably connected to remote electronics, as presently described.

Figure 4:
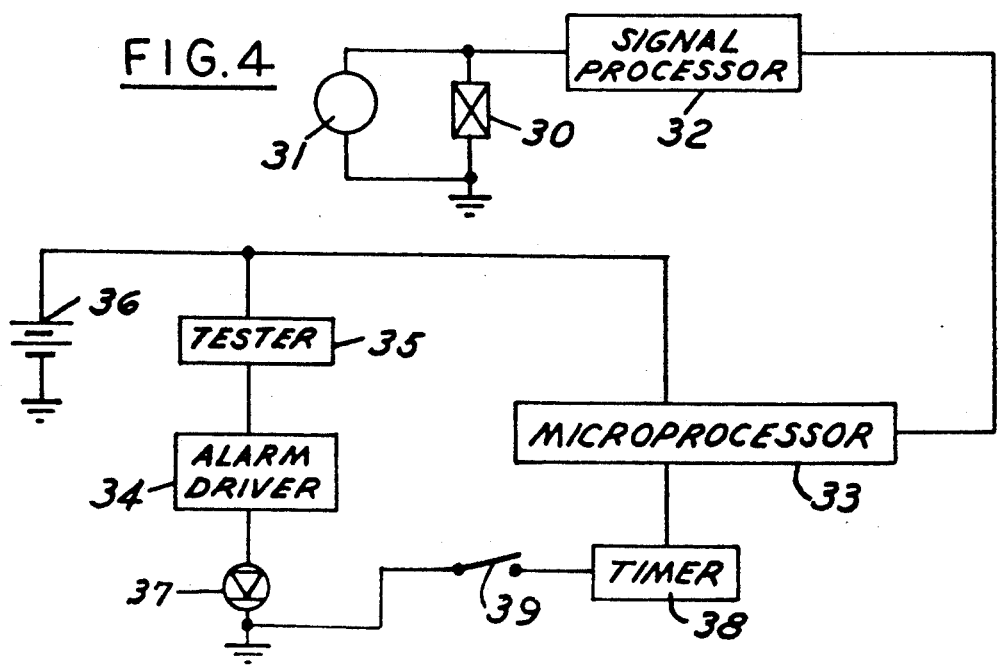
FIG. 4 is a schematic diagram of the electronics utilized in the device.

Referring to FIG. 4, the electronic unit comprises a pressure sensor 30, a driver 31 for energizing the pressure sensor, a signal processor 32 for converting the generated signal from the pressure sensor 30 to proportional digital data which is directed to a microprocessor 33 that processes the data from the pressure variations and determines when the data changes are due to the growth of microorganisms. The device further includes an alarm driver 34, a battery/LED tester 35 for testing the integrity of battery 36 and the alarm indicator 37, a timer 38, and a switch 39.

The presence of organisms in a specimen is detected by microprocessor 33, which employs several pre-set criteria based upon the dynamic characteristics of the absolute value of the rates of change of pressure. These rates depend upon the following parameters:

1. Type of organism (aerobic or anaerobic)
2. Media/Temperature combination (intrinsic properties)
3. Total volume of medium and blood/medium volume ratio
4. Volume of the bottle's head space
5. Pneumatic and electrical variations among components (transducers, internal leaks, needle-septum interface etc.)

These parameters affect the general trend of the rates of change. The microprocessor functions to recognize the relatively wide range of absolute value of the rates and detect microorganisms by their rates of growth. The algorithm, however, does not consider the pressure values and does not make a comparison of these values to a known sample.

Rates can be calculated either locally (time derivative functions) or integrated over longer periods of time. For effective detection local rates are utilized for fast organisms which generate patterns with higher rates. Integrated rates are suitable for slower organisms since a meaningful change is indicated after a longer period of time. In addition the microprocessor functions to recognize either positive or negative rates which relate to generation or consumption of gases in the head space.

The logic of the microprocessor is designed to take into account the wide range of existing absolute values of the rates and to minimize false negative and false positive detections. It combines the following elements:

1. Moving Windows.

A data buffer is allocated in memory for each bottle, if more than one bottle is being tested. This buffer is updated each time a new data point (voltage related to pressure) is measured. The new data point is stored at the last location of the buffer. The rest of the data points in the window which correspond to previous data points are moved by one location while the first location is discarded. The window, therefore, has the most recent history of the curve at each period of time.

2. Multiple Windows

To compensate for the wide variety of the absolute values of the rates of pressure two (or more) windows are utilized simultaneously. These windows may have either different number of data points or data points which are taken at different time intervals. For organisms that respond at fast rates, the total time length of the window is short to detect fast growth which does not last over a long period of time.

3. OR Strategy

The microprocessor employs an OR logic. In other words, if one or more of the window indicates positivity the algorithm flags a positive sample.

4. Integrated Rates

Each time a new data point is collected and the windows are updated, each window rate is determined by subtracting the initial from the final value of the window. This rate is subsequently compared to predetermined rates stored in the computer's memory.

5. Multiple Rates

Several rates are utilized. As an example, the rates associated with two windows:

a. Aerobic organism, short window, positive rate (gas production)
b. Aerobic organism, long window, positive rate
c. Aerobic, short window, negative rate (gas consumption)
d. Aerobic, long window, negative rate
e. Anaerobic, short window, positive rate
f. Anaerobic, long window, positive rate.
Note: In this system, anaerobic organisms do not consume gas and therefore no special windows are allocated for negative rates.

Examples of organisms which correspond to the above rates:
a. *Escherichia coli*
b. *Haemaphilus influenzae*
c. *Acinetobacter antitratus*
d. *Streptococcus pneumoniae*
e. *Clostridium perfringens*
f. *Fusobacterium necrophorum*

For each bottle, a data point is taken at predetermined time intervals. Data points are measured by electrical potential difference (mV) which relate to pressure within the space of the bottle. The collected data points are stored in Random Access Memory (RAM) using "moving window" technique. A moving window is an array of data points which is being updated every time a new data point is collected. Suppose that we have 10 points in a window $X_1, X_2, X_3 \ldots$ where $X_{10}$ is the most recent point. When a new data point X is collected there following operation will follow:

$X_1$ is discarded from the memory
$X_2$ is moved to location $X_1$
$X_3$ is moved to location $X_2$
$X_4$ is moved to location $X_3$
$X_5$ is moved to location $X_4$
$X_6$ is moved to location $X_5$
$X_7$ is moved to location $X_6$
$X_8$ is moved to location $X_7$
$X_9$ is moved to location $X_8$
$X_{10}$ is moved to location $X_9$
the new X is moved to location $X_{10}$ Therefore, each time a new data point is collected the whole data window is moved discarding the oldest point.

Multiple duration windows are utilized to capture the wide range of dynamic curves of slow and fast organisms. A slow organism may not detect on the short window but will detect on the wider one and vice versa. In that respect the detection scheme is an OR condition to minimize false negative detections.

The "moving window" technique allows for dynamic detections which are based upon local absolute values of the rates rather than static measurements based upon amplitude thresholds. In prior existing systems, each collected data point is compared to a reference point which represents the initial pressure. If the difference exceeds a predetermined threshold, a detection is indicated. These static measurements cannot differentiate between slow and fast curves even when these curves do not represent growth of organisms at all. For example, a very moderate change (drift) may occur when white blood cells generate $CO_2$ and thereby increase the pressure at the head space at a very low rate. As a result, a false positive will be detected even though there are no organisms present.

The system does not require that a determination be made as to whether positive pressures or negative (vacuum) conditions are created. An oxygen consuming organism can be detected on positive pressures and a gas producing organism can be detected under vacuum. In other words, the amplitude value of the pressure does not determine detection. Only dynamic changes are required in the "moving" window technique of this system.

After bodily fluid such as blood is drawn and placed in the container by a separate hypodermic needle, the disposable fitment 15 is placed on top of the container 10. The fitment 15 is pressed downwardly and the hypodermic needle 22 penetrates the rubber stopper 12 until the lower end of the sleeve 16 engages the shoulder 14. In this position, the free end of needle 22 is in the headspace above the level of the liquid medium. The electronic unit 27 is then connected to the disposable unit by a locking mechanism. The push button switch 39 is pressed momentarily to reset the electronic device and check the integrity of the battery 36 and the light emitting diode 37 (LED). The LED will turn on if the battery has sufficient energy for at least one test.

Once the reset button is pressed, the electronic circuit is switched to a "sleeping mode" in which minimal energy is drawn from the battery to activate a timer 38 and to keep the information within the memory of the microprocessor 33. After a predetermined amount of time, the timer 38 reactivates the electronic circuit and a pressure magnitude is read by the sensor 30, processed by the signal processor 32 and stored in the memory of the microprocessor as a first value or data point. The initial activation time allows the container which is placed in an incubator to reach its incubation temperature, for example, 35° C. to 37° C.

The electronic circuit is switched by microprocessor back to the "sleeping mode" and the procedure repeats itself at the predetermined time intervals. An alogrithm embedded in the microprocessor determines whether significant pressure rate change has occurred due to presence of organisms. If a positive decision is made, the microprocessor 33 activates the visual LED indicator 37 through the alarm driver 34. This indicator will stay on, regardless of any pressure variations, until the reset switch is pressed again to start a new test.

Figure 6:
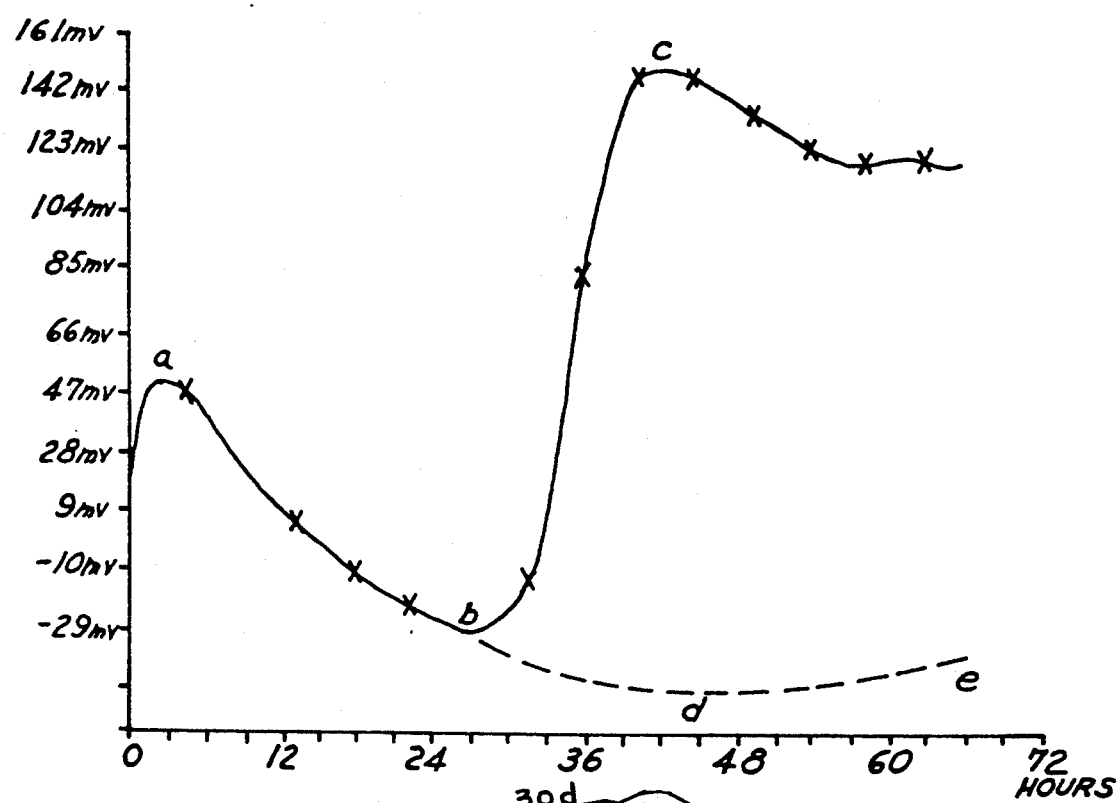
FIG. 6 is a curve of pressure versus time in a typical pressure analysis.

FIG. 6 illustrates a typical pressure-time curve generated by a pressure sensor measuring the developed pressure at the vial's headspace. The initial rise (between time zero and point a) is due to elevation of the vial's temperature from ambient to 35° C. The successive reduction of pressure (interval a to b) is due to reduction of oxygen in the vial's headspace due to oxygen consumption by the medium. If no organism is present, the curve will eventually stabilize at a certain level (vacuum) as illustrated by interval b to d. Later the curve might "drift" slowly upwards from vacuum (negative values) to the atmospheric pressure (zero value) due to a small leakage of air into the vial. If an organism is present, the generated gas results in a sharp increase of pressure as illustrated by the reaction interval b to c. This increase should be detected by the circuit to indicate the presence of microorganisms. Once positive detection is indicated, the alarm light is set on and "detection time" is stored.

Once the reset button is pressed the electronic circuit is switched to a "sleeping mode". In this mode, the electronic circuit can perform limited functions, such as keeping data stored in memory. It may not perform other functions such as data processing. The reason for programming the circuit to a "sleeping mode" is to conserve energy and thereby extend the battery life. In the present case, during the "sleeping" period, data is kept and the electronic timer remains active in order to switch from the "sleeping mode" to a "processing mode" in which the next signal value is taken and processed. The time interval of this "processing mode" is quite small compared to the time interval of the "sleeping mode", for example 1 second in the "processing mode" and 12 minutes in the "sleeping mode". The life of the battery, therefore, can be extended by approximately 1320 fold by utilizing a sleeping/processing scheme.

After the reset button is pressed, after a predetermined time, the timer reactivates the electronic circuit and the first cycle is repeated.

Figure 5:
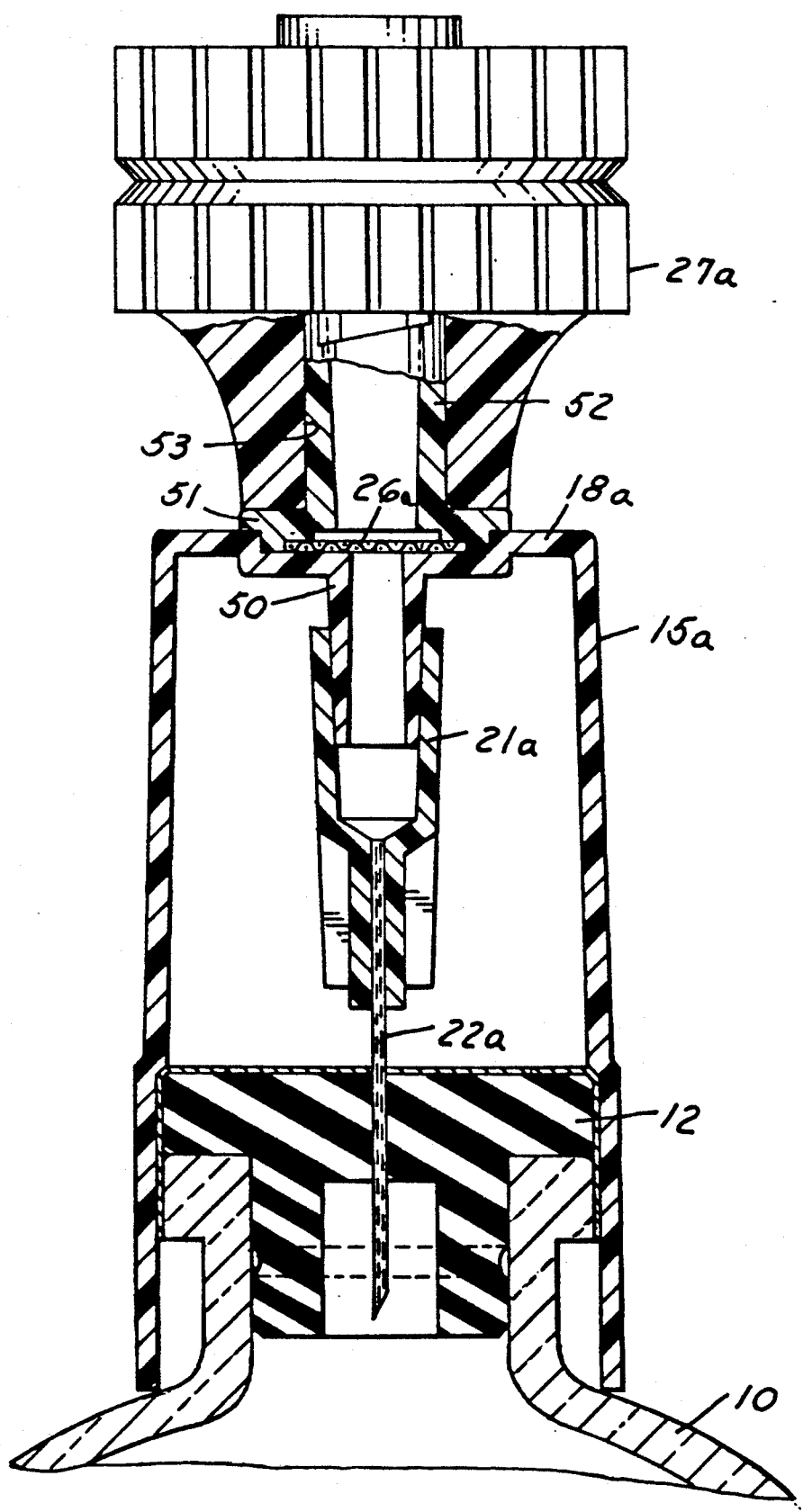
FIG. 5 is a fragmentary sectional view of a modified assembly.

In the modified form of apparatus shown in FIG. 5, the disposable fitment 15a is generally similar to the previously described fitment 15 and includes a top wall 18a having an integral downwardly extending tube 50 that supports the hub 21a of a hypodermic needle 22a. In this form, the hydrophobic vent filter 26a is held in position in the top wall 18a by a fitment 51 that is bonded to the top wall 18a and includes an upwardly extending tubular portion 52. The electronic unit 27a is modified to include a cylindrical recess 53 into which the tubular portion 52 projects exposing the upper end of the needle to the transducer within the electronic unit 27a. In all other respects the assembly is used and functions as described in connection with the form shown in FIGS. 1-3.

Figure 7:
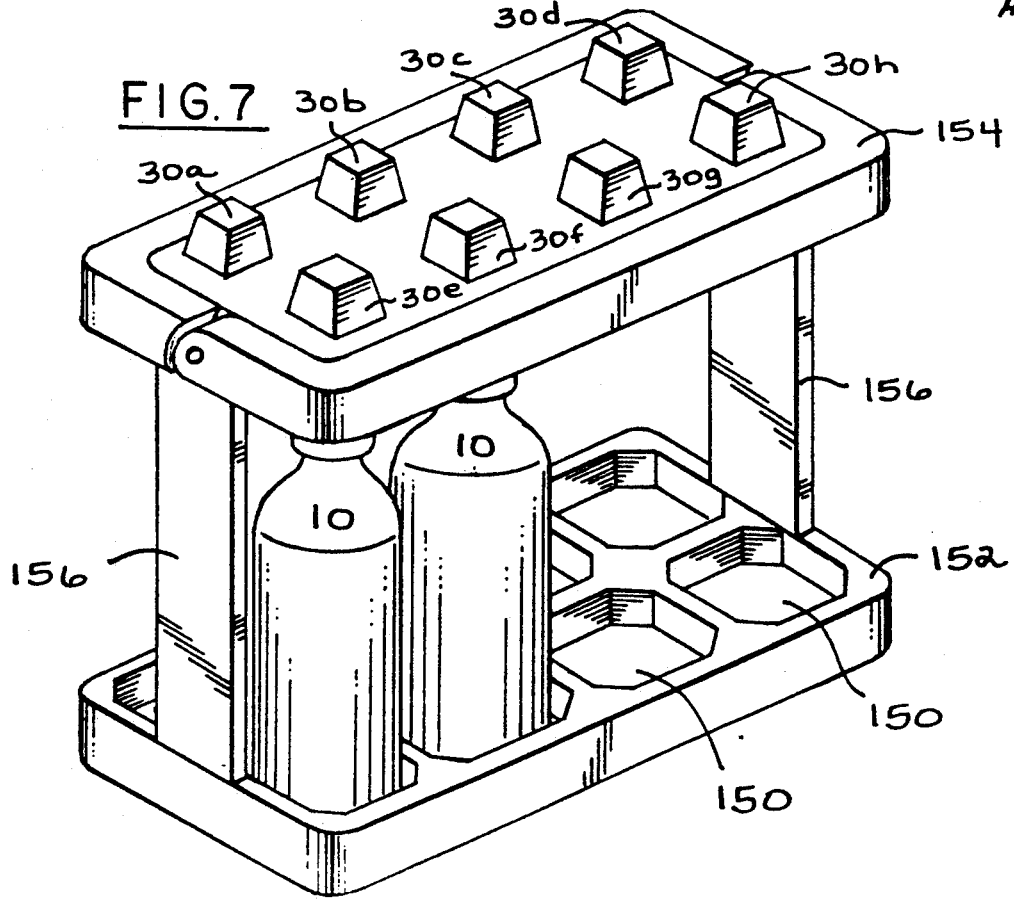
FIG. 7 is a perspective of a modified form of the invention.
Figure 8:
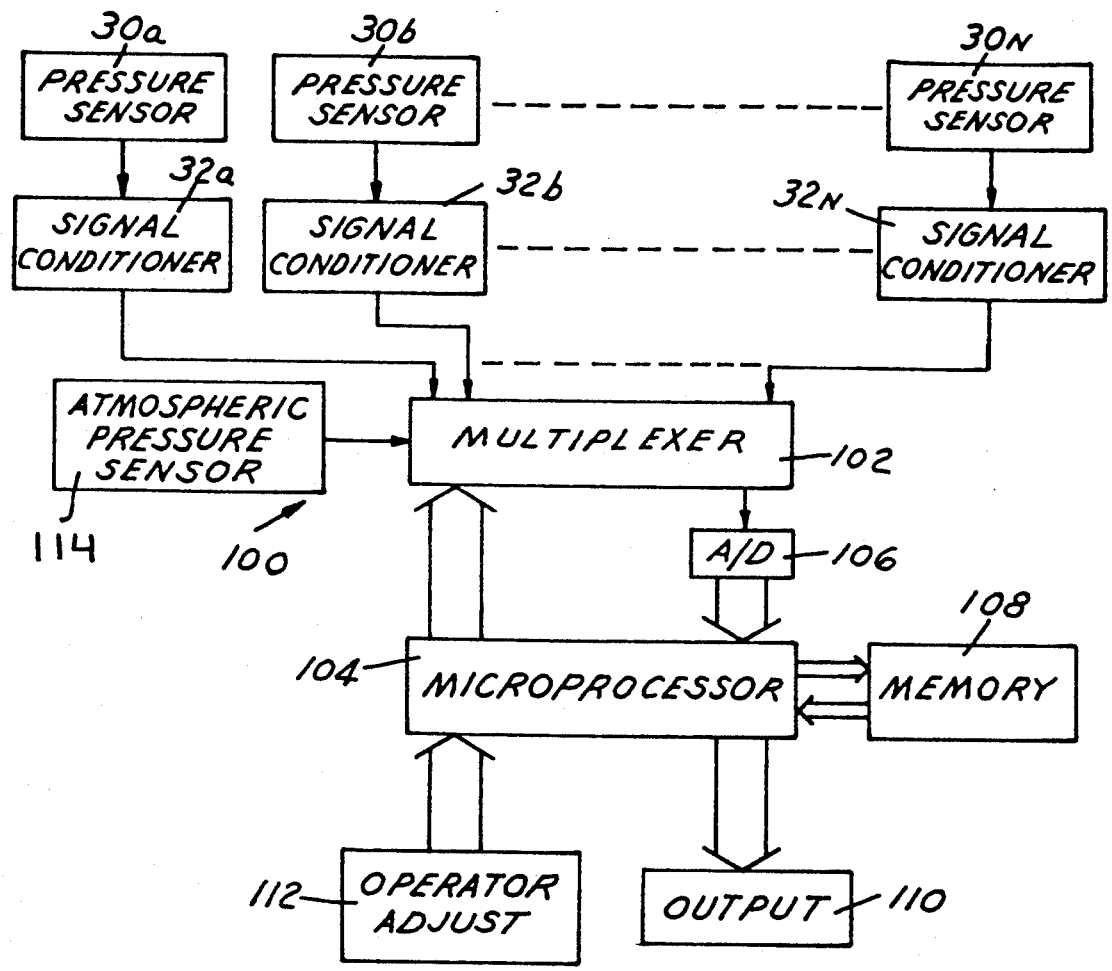
FIG. 8 is a functional block diagram of a system for monitoring growth rates in a plurality of sample containers in accordance with one embodiment of the present invention.

FIG. 8 is a functional block diagram of a system 100 for monitoring a plurality of sample containers 10, such as in FIG. 7, in which a corresponding plurality of pressure sensors 30a-30n are connected through associated signal conditioning circuits 32a-32n to corresponding inputs of a multiplexer 102. Multiplexer 102 is addressable by a microprocessor 104 for selectively reading the electrical pressure sensor signals and feeding the selected signal through an a/d convertor 106 to data input ports of the microprocessor. Sampled signals are stored in sequential locations of a processor memory 108, which may also contain suitable control programming and other operating parameters. Output ports of microprocessor 104 are connected to appropriate output mechanisms 110, such as alarm lights, printers, screens and the like. Microprocessor 104 is also connected to a keyboard or other input device 112 for interaction with the user. Multiplexer 102 also receives a selectable input from a pressure sensor 114, which may be positioned in the incubator chamber for detecting changes in chamber atmosphere pressure. In the event of a radical atmospheric pressure change, indicating breach of the incubator for example, an alarm may be sounded and the test process aborted. Less radical changes in atmospheric pressure may be accommodated by appropriate modification (normalization) of the pressure readings.

In FIG. 7, a plurality of containers 10 are individually received in corresponding depressions or wells 150 of a flat base or tray 152. A top 154, containing a plurality of fitments 15 (FIG. 3) or 15a (FIG. 5) is carried by supports 156 over base 152, with each fitment being aligned with a corresponding well 150. As top 154 is fitted over base 152, the fitments align with containers 10, and the fitment needles pierce the container closures. Pressure sensors herein shown as 30a, 30b, 30c, 30d, 30e, 30f, 30g, 30h, on top 154 are connected by an appropriate cable (not shown) to the remote electronics (FIG. 8).

In operation, the pressure signal from each sensor 30a-30n is sampled at predetermined time intervals, and the sampled pressure signals are stored in associated sequential locations of memory 108. The data so stored for each sensor thus comprises a data array or window of sequential sampled signals. In one implementation of the invention previously summarized, this data array or window may be envisioned as a non-recirculating shift register array in which the oldest data byte is discarded as each new data byte is loaded into the array. Although a dated storage technique of this character is currently preferred for reducing memory requirements, it will be recognized that such operation is not critical to the invention in its broadest aspects, which may be implemented in a microprocessor-based system in which all data is stored for later retrieval and analysis of growth history, etc. if desired.

Rate of sample headspace pressure change, correlating to rate of microbe growth, is determined by subtracting each sampled pressure signal from one or more prestored signals preceding the current signal by a predetermined number of sample increments. For example, in one preferred implementation of the invention, the pressure signals are sampled and stored at six minute increments. Each sampled pressure signal is subtracted from preceding signals for that sensor separated from the current sample by five and ten sample time increments. Thus, in effect, each sample signal is subtracted from corresponding signals obtained thirty minutes and sixty minutes previously. The short comparison window, five sample increments in the present example, detects organisms that exhibit relatively fast growth and corresponding pressure change. On the other hand, the longer comparison window, ten intervals in this example, will detect presence of microbes that exhibit slower growth rates.

Thus, in the preferred implementation of the present invention hereinabove discussed by way of example, each sampled pressure signal is subtracted from two preceding signals, and two growth rates are developed or calculated as a function of differences between the current and preceding sample signals. These rates are then compared with various predetermined standard rates to determine whether microbe growth is indicated in the sample in question. In the presently preferred implementation of the present invention hereinabove discussed, rates are employed to determine presence or absence of growth of microbes of varying types. The standard rates are predetermined empirically as average growth rates for differing families of microorganisms. It has been found that six family growth rates encompass most microorganisms. Average growth rates for each microbe family, but not absolute pressure values or complete pressure curves, are obtained and prestored in memory 108. The initial delay period is determined by the fastest growing microorganism to be detected. For example, for gas-producing aerobic organisms, differing positive rates are employed for the short (first) and long (second) comparison windows (e.g., thirty and sixty minutes respectively). Likewise, third and fourth negative rates are employed for aerobic gas-consuming microbes for the short and long comparison windows respectively. Fifth and sixth positive rates are employed for anaerobic organisms and the short and long comparison windows respectively. In this system, gas consumption by anaerobic organisms is not present, and therefore no corresponding rates are allocated for anaerobic negative growth pressure rates. If the absolute mathematical value of the rate of pressure change in the sample under test exceeds the absolute mathematical value of any of the stored rates, presence of a microbe is indicated and an alarm is correspondingly activated. In this connection, it will be appreciated that the test procedure of the present invention is qualitative—i.e., presence of a microorganism is determined but no effort is made to establish concentration. In the same way, no effort is made to establish either the family or type of microorganism. These determinations can be made in other procedures, if desired. The present invention seeks merely to determine presence of a microorganism, regardless of type or concentrations.

FIGS. 9-16 illustrate detection of various microbe growths and growth rates in accordance with other presently preferred implementations of the invention. In each FIG. 9-16, pressure sensor output in pressure (millivolts) is plotted against time in hours. Differing test parameters (e.g., sampling interval, long and short windows) are employed, as will be described in conjunction with each figure. No sample readings were taken during an initial (programmable) period to allow stabilization to incubator temperature and initiation of microbe growth. It will be recognized that the foregoing and other test parameters may be varied by operator adjustment mechanism 112 (FIG. 8) or the like.

Figure 11:
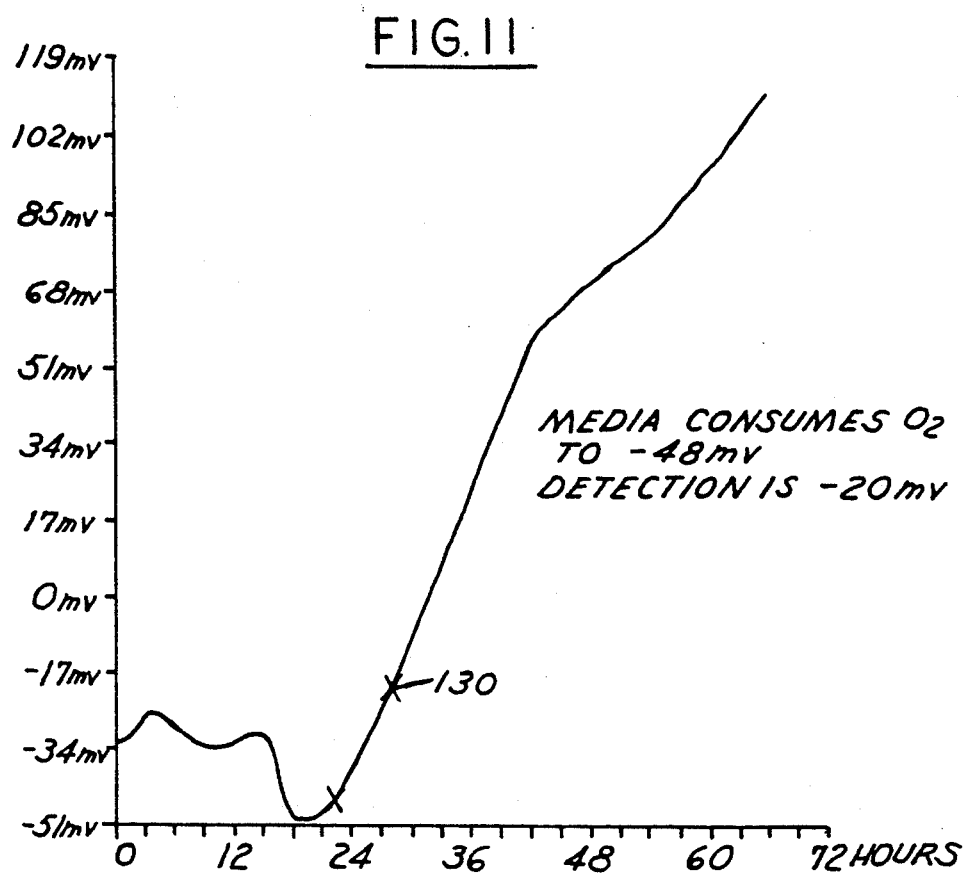

FIG. 9 illustrates short-window detection of a gas-producing microbe. After an initial wait or delay period of three hours, the pressure signal is sampled and stored at twelve minute increments. The short and long window rates were set at pressure (ten millivolts)—i.e., a ten millivolt change between the current sampled signal and the preceding signal to what it is compared. The short window was seventy-two minutes or six sampling intervals, and the long window was two hours or ten sampling intervals. After 1.6 hours—i.e., 4.6 hours from initiation of the test—presence of a microbe is indicated at point 120. The high positive rate or slope of pressure change between point 120 and the reading taken at point 122 five samples earlier exceeded the corresponding short-window detection rate. Likewise, in FIG. 10, the initial reading after the three-hour delay is taken at point 124. Thereafter, each reading indicates a negative rate or slope up to point 126 at about nine hours. However, this negative slope does not exceed the negative or gas-consumption rates. After nine hours, a positive or gas-producing rate of pressure change is detected at point 128, a total of 10.4 hours after initiation of the test. FIG. 11 illustrates long-window detection of a gas-producing microbe. Long-window (120 minute) detection at point 130 indicates growth of a corresponding microbe.

Figure 12:
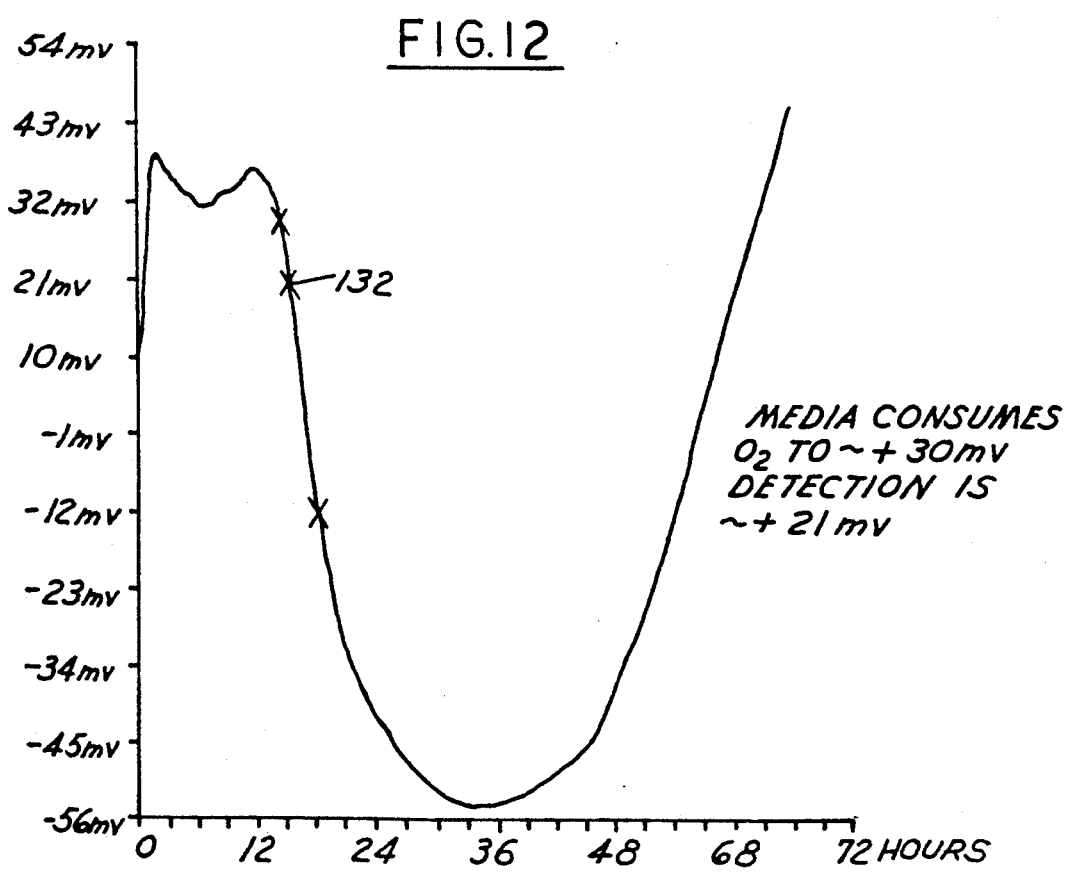

FIGS. 12-14 illustrate detection of gas-consuming or negative-rate microbes at a short detection window of 120 minutes (FIGS. 12 and 14) and long detection windows of 144 minutes (FIG. 13). In each of the FIGS. 12-14, the initial shutdown period was 180 minutes, and the sampling interval was 12 minutes. The detection thresholds were ten millivolts in each case. Presence of microbes were detected at points 132, 134 and 136 respectively.

FIGS. 15 and 16 illustrate detection of gas-producing microbes. In each of the FIGS. 15 and 16, the initial shutdown was 360 minutes, the sampling interval was 24 minutes, the short-window detection time was 96 minutes, the long-window detection time was 336 minutes, the short positive detection threshold was seven millivolts and the long positive detection threshold was five millivolts. Short-window detection took place at point 138 in FIG. 15, and long-window detection took place at point 140 in FIG. 16.

There are thus provided a method and apparatus for detecting microbe growth that satisfy all of the objects and aims previously set forth. The disposable fitments illustrated in FIGS. 1-3 and 5 are economical to manufacture and use. Note that, in each embodiment, the outer sleeve has an axial dimension greater than that of the needle, to help protect the user. Filters 26, 26a protect against emission of fluid under pressure upon initial insertion of the needle.

The electronics (FIGS. 4 and 8) features comparison of rates of absolute values of the pressure change, as distinguished from absolute values of actual pressure, which may be subject to error due to ambient temperature and pressure fluctuations, as well as other factors. Rate of pressure change of each sample over short and/or long time intervals is compared with predetermined standard rates empirically determined for families of microorganisms.

Avoidance of attempts to determine specific microbe type and/or concentration greatly simplifies the process and hardware.

The method and apparatus also feature wide adjustability to accommodate differing environments and conditions. Atmospheric conditions in the incubation chamber are automatically accommodated. Both oxygen-consuming and oxygen-producing microbes are detected, as are microbes having differing growth rates. The electronics, including the pressure sensor, may be economically packaged for removable coupling to a disposable fitment that may be assembled to the test container. In this connection, the electronics is isolated from the fluids, and may be repeatedly reused with fresh fitments. In another embodiment of the invention, remote electronics may receive signals from a plurality of pressure sensors, each of which is removably affixed to the fitment on a test container.

We claim:

1. A method of detecting microbiological growth in a sealed sample container which contains a bodily fluid which may contain an unknown microorganism, said method comprising the steps of:
    (a) providing a sealed sample container which contains a bodily fluid,
    (b) monitoring pressure changes within a headspace of the sealed sample container,
    (c) detecting absolute value of rate of change of said headspace pressure, and
    (d) indicating a presence of microbiological growth within the sealed sample container as a function of such absolute value of rate of change of said headspace pressure.

2. The method set forth in claim 1 wherein said step (b) comprises the step of positioning a pressure sensor in operative communication with the headspace so as to develop an electronic pressure signal that varies as a function of said headspace pressure.

3. The method set forth in claim 1 wherein said step (c) comprises the steps of:
    (b1) sampling the head pressure at predetermined time intervals,
    (b2) storing the samples developed in said step (b1), and (b3) subtracting successive samples from each other to determine said absolute value of rate of change.

4. The method set forth in claim 3 wherein said step (b3) comprises the step of subtracting each of said samples in said step (b1) from a sample previously stored in said step (b2).

5. The method set forth in claim 3 wherein said step (b3) comprises the step of subtracting each samples in said step (b1) from at least two samples previously stored in said step (b2).

6. The method set forth in claim 3 comprising the additional step of delaying said step (b1) to permit onset of biological activity in said sealed sample container prior to initially sampling the head pressure and storing the pressure samples.

7. A method of detecting presence of microorganisms in a test sample which contains a bodily fluid which may contain an unknown microorganism, said method comprising the steps of:
 (a) placing a test sample which contains a bodily fluid in a closed container with a growth medium leaving a headspace over said growth medium,
 (b) coupling an electronic pressure sensor to said closed container so as to provide an electric pressure signal as a function of gas pressure change in said headspace,
 (c) successively sampling and storing said electric pressure signal,
 (d) subtracting successive sampled pressure signals from each other to determine absolute value of rate of change of pressure in said headspace,
 (e) comparing absolute value of rate of change determined in said step (d) with preselected rates of change of pressure corresponding to a plurality of microorganisms which include gas producing microorganisms, and gas consuming microorganisms which have varying rates of growth, and
 (f) indicating a presence of microorganisms in the test sample when said absolute value of rate of change determined in said step (d) exceeds one of a plurality of preselected rates of change of pressure.

8. The method set forth in claim 7 wherein said step (d) comprises the step of subtracting each said electric pressure signal sampled in said step (c) from at least two of said signals sampled and stored previously so as to determine rates of change over time, and
 wherein said step (e) comprises the step of comparing said absolute vale of rates of change determined in said step (d) to differing preselected rates of change of pressure.

9. The method set forth in claim 8 wherein said step (f) comprises the step of indicating presence of microorganisms in the test sample when the absolute value of rate of change determined in said step (d) exceeds the corresponding preselected rate of change of pressure to which it is compared in said step (e).

10. The method set forth in claim 9 wherein at least one of said plurality of preselected rates of change is a negative rate of change of pressure.

11. Apparatus for detecting microbiological growth in a sealed container having a headspace and which contains a bodily fluid which may contain an unknown microorganism, said apparatus comprising:
 pressure sensing means including an electronic pressure sensor and means for coupling said electronic pressure sensor to a container so as to provide an electric signal as a function of gas pressure change in the headspace of the container,
 means for sequentially sampling and storing said electrical signal, means for subtracting successive sampled stored electrical signals from each other for determining absolute means of rate of change of pressure in the container headspace,
 said sampling-and-storing means comprising a memory having sequential storage locations and means for storing said successive sample stored electrical signals in said memory in sequence by sampling increment, and
 means for indicating microbiological growth as a function of said absolute means of stored rates of change.

12. The apparatus as set forth in claim 11 wherein said means for subtracting said electrical signals comprises means for subtracting each said successive sample stored electrical signal from a successive sample stored electrical signal stored in said memory at a location corresponding to preceding increments of time.

13. The apparatus as set forth in claim 12 wherein said subtracting means comprises means for subtracting each said successive sample stored electrical signal from at least two successive sample stored electrical signals stored in said memory at locations corresponding to preceding increments of time.

14. The apparatus set forth in claim 11 wherein said growth-indicating means comprises means for comparing the absolute value of said rate of change of pressure to a preselected rate of change of pressure, and means for indicating growth when said absolute value exceeds said preselected rate of change of pressure.

15. The apparatus set forth in claim 14 wherein said growth-indicating means comprises means for comparing said absolute value of rate of change of pressure to at least two preselected differing rates of change of pressure, and means for indicating growth when said absolute value exceeds either of said preselected rates of change of pressure.

16. The apparatus set forth in claim 15 wherein at least one of said preselected rates of change of pressure is negative, and wherein said indicating means comprise means for indicating growth when the absolute value of said rate of change pressure exceeds the absolute value of said negative rate of change of pressure.

17. The apparatus set forth in claim 11 wherein said sampling-and-storing means, said subtracting means and said indicating means collectively comprise a programmed microprocessor.

18. The apparatus set forth in claim 17 comprising a plurality of said electronic pressure sensors with associated means for coupling each said electric pressure sensor to a sample container, and multiplexing means coupling said plurality of electronic pressure sensors to said programmed microprocessor for selectively reading pressure signals from said electronic pressure sensors.

19. A method of detecting microbiological growth in a sealed sample container having a headspace and which contains a bodily fluid which may contain an unknown microorganism, said method comprising the steps of:
 (a) providing a sealed sample container having a headspace and which contains a bodily fluid,
 (b) monitoring pressure within headspace of the container,
 (c) calculating absolute value of rate of change of said headspace pressure, and (d) comparing the absolute value of the rate of change of headspace pressure with a plurality of rates for a plurality of microorganisms which include gas producing microorganisms, gas consuming microorganisms and microorganisms having varying growth rates.

20. Apparatus for detecting microbiological growth in a sealed container having a headspace and which contains a bodily fluid which may contain an unknown microorganisms, said apparatus comprising:

pressure sensing means including an electronic pressure sensor and means for coupling said electronic pressure sensor to a container so as to provide an electrical signal as a function of gas pressure change in the headspace of the container, means for sequentially sampling and storing said electric signal at periodic time intervals, means for subtracting successive sampled and stored electric signals from each other for determining absolute value of rate of change of pressure in the container headspace, and means for detecting the presence of a microorganism by comparing said absolute rate of change of pressure with the rates of change of pressure corresponding to a plurality of microorganisms which include gas producing microorganisms, gas consuming microorganisms and microorganisms having varying rates of growth.

* * * * *